US012575603B2

(12) United States Patent
Hubbard et al.

(10) Patent No.: US 12,575,603 B2
(45) Date of Patent: *Mar. 17, 2026

(54) AEROSOL DELIVERY DEVICE WITH MULTIPLE AEROSOL DELIVERY PATHWAYS

(71) Applicant: RAI STRATEGIC HOLDINGS, INC., Winston-Salem, NC (US)

(72) Inventors: Sawyer Hubbard, Winston-Salem, NC (US); Eric Taylor Hunt, Pfafftown, NC (US); Karen V. Taluskie, Winston-Salem, NC (US); Stephen Benson Sears, Siler City, NC (US); Donna Walker Duggins, Winston-Salem, NC (US); Michael F. Davis, Clemmons, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,484

(22) Filed: Oct. 18, 2023

(65) Prior Publication Data

US 2024/0065318 A1 Feb. 29, 2024

Related U.S. Application Data

(63) Continuation of application No. 17/005,886, filed on Aug. 28, 2020, now Pat. No. 11,819,055, which is a (Continued)

(51) Int. Cl.
*A24F 40/30* (2020.01)
*A24F 40/485* (2020.01)
(Continued)

(52) U.S. Cl.
CPC ............ *A24F 40/30* (2020.01); *A24F 40/485* (2020.01); *A61M 11/042* (2014.02);
(Continued)

(58) Field of Classification Search
CPC .......... A24F 40/30; A24F 40/40; A24F 40/42; A24F 40/485
See application file for complete search history.

(56) References Cited

U.S. PATENT DOCUMENTS 2,033,909 A 3/1936 Cox
2,057,353 A 10/1936 Whittemore, Jr.
(Continued)

FOREIGN PATENT DOCUMENTS

CN 1541577 11/2004
CN 2719043 8/2005
(Continued)

OTHER PUBLICATIONS

Notice of Allowance issued Aug. 6, 2025, in corresponding Korean Application No. 10-2024-7011038.

*Primary Examiner* — Hae Moon Hyeon
(74) *Attorney, Agent, or Firm* — Womble Bond Dickinson (US) LLP

(57) ABSTRACT

The present disclosure relates to aerosol delivery devices and related methods of delivering aerosol to a user. The aerosol delivery devices include a housing providing multiple aerosol pathways having a mouth-end opening through which aerosol can be inhaled by a user, the housing defining a first aerosol delivery pathway in fluid communication with the mouth-end opening and a second aerosol delivery pathway separate from the first aerosol delivery pathway and in fluid communication with the mouth-end opening. An atomizer including a heating element or piezoelectric element and a liquid transport element in fluid communication with an
(Continued)

aerosol precursor composition is provided in fluid communication with the first aerosol delivery pathway. A flavorant-infused material is positioned within the second aerosol delivery pathway and adapted to produce a second aerosol upon contact between the flavorant-infused material and flowing air.

23 Claims, 6 Drawing Sheets

Related U.S. Application Data continuation of application No. 15/843,497, filed on Dec. 15, 2017, now Pat. No. 10,786,010.

(51) Int. Cl.

| | |
|---|---|
| *A61M 11/04* | (2006.01) |
| *A61M 15/06* | (2006.01) |
| *H05B 3/06* | (2006.01) |
| *A24F 40/10* | (2020.01) |
| *A24F 40/20* | (2020.01) |
| *A61M 15/00* | (2006.01) |

(52) U.S. Cl.
CPC .............. *A61M 15/06* (2013.01); *H05B 3/06* (2013.01); *A24F 40/10* (2020.01); *A24F 40/20* (2020.01); *A61M 15/0003* (2014.02); *A61M 15/0021* (2014.02); *A61M 2205/3653* (2013.01); *A61M 2205/8206* (2013.01); *H05B 2203/021* (2013.01)

(56) References Cited

U.S. PATENT DOCUMENTS

| | | | |
|---|---|---|---|
| 2,104,266 A | 1/1938 | McCormick | |
| 3,200,819 A | 8/1965 | Gilbert | |
| 3,901,248 A | 8/1975 | Lichneckert et al. | |
| 4,735,217 A | 4/1988 | Gerth et al. | |
| 4,922,901 A | 5/1990 | Brooks et al. | |
| 4,947,874 A | 8/1990 | Brooks et al. | |
| 4,947,875 A | 8/1990 | Brooks et al. | |
| 5,060,671 A | 10/1991 | Counts et al. | |
| 5,093,894 A | 3/1992 | Deevi et al. | |
| 5,101,839 A | 4/1992 | Jakob et al. | |
| 5,105,831 A | 4/1992 | Banerjee et al. | |
| 5,154,192 A | 10/1992 | Sprinkel et al. | |
| 5,159,942 A | 11/1992 | Brinkley et al. | |
| 5,224,498 A | 7/1993 | Deevi et al. | |
| 5,228,460 A | 7/1993 | Sprinkel et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,372,148 A | 12/1994 | McCafferty et al. | |
| 5,388,574 A | 2/1995 | Ingebrethsen et al. | |
| 5,388,594 A | 2/1995 | Counts et al. | |
| 5,468,936 A | 11/1995 | Deevi et al. | |
| 5,498,850 A | 3/1996 | Das | |
| 5,498,855 A | 3/1996 | Deevi et al. | |
| 5,530,225 A | 6/1996 | Hajaligol | |
| 5,573,692 A | 11/1996 | Das et al. | |
| 5,591,368 A | 1/1997 | Fleischhauer et al. | |
| 5,659,656 A | 8/1997 | Das | |
| 5,665,262 A | 9/1997 | Hajaligol et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,865,185 A | 2/1999 | Collins et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |

| | | | |
|---|---|---|---|
| 6,040,560 A | 3/2000 | Fleischhauer et al. | |
| 6,053,176 A | 4/2000 | Adams et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,772,756 B2 | 8/2004 | Shayan | |
| 6,803,545 B2 | 10/2004 | Blake et al. | |
| 6,810,883 B2 | 11/2004 | Felter et al. | |
| 6,854,461 B2 | 2/2005 | Nichols et al. | |
| 7,040,314 B2 | 5/2006 | Nguyen et al. | |
| 7,117,867 B2 | 10/2006 | Cox et al. | |
| 7,293,565 B2 | 11/2007 | Griffin et al. | |
| 7,479,098 B2 | 1/2009 | Thomas et al. | |
| 7,513,253 B2 | 4/2009 | Kobayashi et al. | |
| 7,647,932 B2 | 1/2010 | Cantrell et al. | |
| 7,726,320 B2 | 6/2010 | Robinson et al. | |
| 7,811,587 B2 | 10/2010 | Donovan | |
| 7,832,410 B2 | 11/2010 | Hon | |
| 7,833,146 B2 | 11/2010 | Deal | |
| 7,896,006 B2 | 3/2011 | Hamano et al. | |
| 7,972,254 B2 | 7/2011 | Stokes et al. | |
| 7,984,719 B2 | 7/2011 | Dube et al. | |
| 8,079,371 B2 | 12/2011 | Robinson et al. | |
| 8,156,944 B2 | 4/2012 | Han | |
| 8,186,359 B2 | 5/2012 | Ademe et al. | |
| 8,205,622 B2 | 6/2012 | Pan | |
| 8,262,550 B2 | 9/2012 | Barnes et al. | |
| 8,314,591 B2 | 11/2012 | Terry et al. | |
| 8,353,810 B2 | 1/2013 | Cieslikowski et al. | |
| 8,365,742 B2 | 2/2013 | Hon | |
| 8,375,957 B2 | 2/2013 | Hon | |
| 8,381,947 B2 | 2/2013 | Garthaffner et al. | |
| 8,402,976 B2 | 3/2013 | Fernando et al. | |
| 8,459,272 B2 | 6/2013 | Karles et al. | |
| 8,470,215 B2 | 6/2013 | Zhang | |
| 8,499,766 B1 | 8/2013 | Newton | |
| 8,678,013 B2 | 3/2014 | Crooks et al. | |
| 8,689,804 B2 | 4/2014 | Fernando et al. | |
| 8,695,609 B2 | 4/2014 | Dube et al. | |
| 8,739,802 B2 | 6/2014 | Fagg | |
| 8,794,231 B2 | 8/2014 | Thorens et al. | |
| 8,851,083 B2 | 10/2014 | Oglesby et al. | |
| 8,881,737 B2 | 11/2014 | Collett et al. | |
| 8,905,243 B2 | 12/2014 | Dixon et al. | |
| 8,910,639 B2 | 12/2014 | Chang et al. | |
| 8,915,254 B2 | 12/2014 | Monsees et al. | |
| 8,925,555 B2 | 1/2015 | Monsees et al. | |
| 9,220,302 B2 | 12/2015 | DePiano et al. | |
| 9,254,002 B2 | 2/2016 | Chong et al. | |
| 9,573,147 B1 | 2/2017 | Yeates et al. | |
| 9,888,723 B2 | 2/2018 | Cameron et al. | |
| 10,470,491 B2 | 11/2019 | Sutton et al. | |
| 10,492,526 B2 | 12/2019 | Sampson et al. | |
| 10,786,010 B2 * | 9/2020 | Hubbard | A61M 11/042 |
| 10,980,283 B2 | 4/2021 | Alelov | |
| 11,213,635 B2 | 1/2022 | Hepworth et al. | |
| 11,253,000 B2 | 2/2022 | Hepworth et al. | |
| 11,318,264 B2 * | 5/2022 | Yilmaz | A61M 11/042 |
| 11,504,486 B2 * | 11/2022 | Gallagher | A61M 11/042 |
| 11,819,055 B2 * | 11/2023 | Hubbard | A61M 15/06 |
| 2004/0173229 A1 | 9/2004 | Crooks et al. | |
| 2004/0191322 A1 | 9/2004 | Hansson | |
| 2005/0016550 A1 | 1/2005 | Katase | |
| 2005/0066986 A1 | 3/2005 | Nestor et al. | |
| 2006/0081721 A1 | 4/2006 | Caserta et al. | |
| 2006/0196518 A1 | 9/2006 | Hon | |
| 2007/0119450 A1 | 5/2007 | Wharton et al. | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0272379 A1 | 11/2009 | Thorens et al. | |
| 2010/0024834 A1 | 2/2010 | Oglesby et al. | |
| 2010/0028766 A1 | 2/2010 | Peckerar et al. | |
| 2010/0184576 A1 | 7/2010 | Prestia et al. | |
| 2010/0186757 A1 | 7/2010 | Crooks et al. | |
| 2010/0307518 A1 | 12/2010 | Wang | |
| 2011/0053745 A1 | 3/2011 | Iliev et al. | |

(56) References Cited

U.S. PATENT DOCUMENTS

| | | |
|---|---|---|
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0268809 A1 | 11/2011 | Brinkley et al. |
| 2011/0271968 A1 | 11/2011 | Carpenter et al. |
| 2011/0271971 A1 | 11/2011 | Conner et al. |
| 2011/0290248 A1 | 12/2011 | Schennum |
| 2012/0042885 A1 | 2/2012 | Stone et al. |
| 2012/0067360 A1 | 3/2012 | Conner et al. |
| 2012/0111347 A1 | 5/2012 | Hon |
| 2012/0245007 A1 | 9/2012 | Henley et al. |
| 2012/0255569 A1 | 10/2012 | Beard et al. |
| 2012/0260927 A1 | 10/2012 | Liu |
| 2012/0279512 A1 | 11/2012 | Hon |
| 2013/0008457 A1 | 1/2013 | Zheng et al. |
| 2013/0037041 A1 | 2/2013 | Worm et al. |
| 2013/0056013 A1 | 3/2013 | Terry et al. |
| 2013/0085052 A1 | 4/2013 | Novak, III et al. |
| 2013/0255702 A1 | 10/2013 | Griffith, Jr. et al. |
| 2013/0306084 A1 | 11/2013 | Flick |
| 2013/0319404 A1 | 12/2013 | Feriani et al. |
| 2014/0000638 A1 | 1/2014 | Sebastian et al. |
| 2014/0053855 A1 | 2/2014 | Hartmann et al. |
| 2014/0060554 A1 | 3/2014 | Collett et al. |
| 2014/0060555 A1 | 3/2014 | Chang et al. |
| 2014/0060556 A1 | 3/2014 | Liu |
| 2014/0096781 A1 | 4/2014 | Sears et al. |
| 2014/0096782 A1 | 4/2014 | Ampolini et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261488 A1 | 9/2014 | Tucker |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2015/0020823 A1 | 1/2015 | Lipowicz et al. |
| 2015/0020830 A1 | 1/2015 | Koller |
| 2015/0027454 A1 | 1/2015 | Li et al. |
| 2015/0047662 A1 | 2/2015 | Hopps |
| 2015/0059780 A1 | 3/2015 | Davis et al. |
| 2015/0114409 A1 | 4/2015 | Brammer et al. |
| 2015/0173422 A1 | 6/2015 | Liu |
| 2015/0223521 A1 | 8/2015 | Menting et al. |
| 2015/0283070 A1 | 10/2015 | Stenzler et al. |
| 2015/0335070 A1 | 11/2015 | Sears et al. |
| 2015/0335071 A1 | 11/2015 | Brinkley et al. |
| 2016/0073695 A1 | 3/2016 | Sears et al. |
| 2016/0089508 A1* | 3/2016 | Smith ............... A61M 15/0085 |
| | | 128/202.21 |
| 2016/0206005 A1 | 7/2016 | Yamada et al. |
| 2016/0227839 A1 | 8/2016 | Zuber et al. |
| 2016/0235121 A1 | 8/2016 | Rogan et al. |
| 2016/0295914 A1 | 10/2016 | Jordil et al. |
| 2016/0302487 A1 | 10/2016 | Chen |
| 2016/0331034 A1* | 11/2016 | Cameron .......... A61M 15/0003 |
| 2016/0360785 A1 | 12/2016 | Bless et al. |
| 2016/0366946 A1 | 12/2016 | Murison et al. |
| 2017/0071251 A1* | 3/2017 | Goch .................... A24F 40/485 |
| 2017/0096291 A1 | 4/2017 | Gardner |
| 2017/0127722 A1 | 5/2017 | Davis et al. |
| 2017/0157341 A1* | 6/2017 | Pandya ............... A61M 11/042 |
| 2017/0181471 A1 | 6/2017 | Phillips et al. |
| 2017/0188626 A1 | 7/2017 | Davis et al. |
| 2017/0250552 A1 | 8/2017 | Liu |
| 2017/0258139 A1* | 9/2017 | Rostami ................. G06F 1/189 |
| 2017/0304561 A1 | 10/2017 | Hazani |
| 2017/0325505 A1 | 11/2017 | Force et al. |
| 2018/0209542 A1 | 7/2018 | Chen |
| 2018/0228217 A1 | 8/2018 | Mironov et al. |
| 2019/0183177 A1 | 6/2019 | Hubbard et al. |
| 2019/0254344 A1 | 8/2019 | Hepworth et al. |
| 2020/0376208 A1 | 12/2020 | Spencer et al. |
| 2020/0390150 A1 | 12/2020 | Hubbard et al. |
| 2020/0404963 A1 | 12/2020 | Rostami et al. |

FOREIGN PATENT DOCUMENTS

| | | |
|---|---|---|
| CN | 1764704 A | 4/2006 |
| CN | 101043827 A | 9/2007 |
| CN | 201379072 | 1/2010 |
| CN | 103544907 A | 1/2014 |
| CN | 203407519 U | 1/2014 |
| CN | 103783672 A | 5/2014 |
| CN | 203692553 U | 7/2014 |
| CN | 203776160 U | 8/2014 |
| CN | 204245158 U | 4/2015 |
| CN | 205052884 U | 3/2016 |
| CN | 205390305 U | 7/2016 |
| CN | 205611789 U | 10/2016 |
| CN | 206284401 U | 6/2017 |
| CN | 107054864 A | 8/2017 |
| CN | 206687167 U | 12/2017 |
| EP | 0 295 122 | 12/1988 |
| EP | 0 845 220 | 6/1998 |
| EP | 1 618 803 | 1/2006 |
| EP | 2989 912 | 3/2016 |
| GB | 2469850 | 11/2010 |
| GB | 2529201 A | 2/2016 |
| KR | 1020170128492 A | 11/2017 |
| SU | 935069 A1 | 6/1982 |
| UA | 67598 U | 2/2012 |
| WO | WO 03/009711 | 2/2003 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2010/003480 | 1/2010 |
| WO | WO 2010/091593 | 8/2010 |
| WO | 2011129677 A1 | 10/2011 |
| WO | WO 2013/089551 | 6/2013 |
| WO | 2013127810 A1 | 9/2013 |
| WO | WO 2014/170947 | 10/2014 |
| WO | WO 2014/182736 | 11/2014 |
| WO | WO 2015/079197 | 6/2015 |
| WO | 2016107762 A1 | 7/2016 |

* cited by examiner

AEROSOL DELIVERY DEVICE WITH MULTIPLE AEROSOL DELIVERY PATHWAYS

CROSS-REFERENCE TO RELATED APPLICATIONS

This application is a continuation of U.S. application Ser. No. 17/005,886, filed Aug. 28, 2020, which is a continuation of U.S. application Ser. No. 15/843,497, filed Dec. 15, 2017, both of which are incorporated herein by reference in their entirety and for all purposes.

BACKGROUND

Field of the Disclosure

The present disclosure relates to aerosol delivery devices, such as electronic cigarettes, and more particularly to aerosol delivery devices including an atomizer. The atomizer may be configured to heat an aerosol precursor composition, which may be made or derived from tobacco or otherwise incorporate tobacco, to form an inhalable substance for human consumption.

Description of Related Art

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

Many electronic cigarette products comprise an atomizer with a "wick/coil" design, which includes an electrical resistance heater wire wrapped around a fibrous wicking material. Such a design has potential drawbacks with respect to delivery of flavorants adapted to alter the sensory characteristics of aerosol produced by the device. For example, flavorant compounds can be temperature-sensitive and subject to thermal decomposition if heated above a given temperature, which can negatively impact the sensory experience associated with the aerosol. Accordingly, there remains a need in the art for aerosol delivery devices that deliver a desirable and consistent sensory experience.

BRIEF SUMMARY OF THE DISCLOSURE

The present disclosure relates to an atomizer for aerosol delivery devices configured to produce aerosol and which aerosol delivery devices, in some embodiments, may be referred to as electronic cigarettes. In one aspect, an aerosol delivery device is provided that comprises a housing providing multiple aerosol pathways having a mouth-end opening through which aerosol can be inhaled by a user, the housing defining a first aerosol delivery pathway in fluid communication with the mouth-end opening and a second aerosol delivery pathway separate from the first aerosol delivery pathway and in fluid communication with the mouth-end opening. The device further includes a reservoir containing a liquid aerosol precursor composition, an atomizer comprising a heating element (e.g., electrical resistance heating element, inductive heating element, infrared heating element, and the like) or piezoelectric element and a liquid transport element in fluid communication with the reservoir and in fluid communication with the heating element or piezoelectric element, the atomizer adapted to produce a first aerosol from the aerosol precursor composition, the atomizer positioned in fluid communication with the first aerosol delivery pathway, wherein the atomizer is in fluid communication with a first air inlet. The device further includes a flavorant-infused material positioned within the second aerosol delivery pathway and adapted to produce a second aerosol upon contact between the flavorant-infused material and flowing air, the flavorant-infused material positioned in fluid communication with a second air inlet.

In some embodiments, the housing further defines a mixing area downstream from the first and second aerosol delivery pathways and adapted to allow mixing of the first and second aerosols prior to exit from the mouth-end opening. The device may further include a heater positioned to heat at least a portion of the flavorant-infused material positioned within the second aerosol delivery pathway. Advantageously, the first aerosol may be respirable and the second aerosol may be non-respirable.

In certain embodiments, the liquid aerosol precursor composition is substantially flavorant-free. Examples of the flavorant-infused material include a liquid solution or emulsion comprising a liquid carrier and a flavorant admixed with the liquid carrier, or a substrate and a releasable flavorant carried by the substrate. Exemplary flavorant-infused materials are in the form of one or more porous monoliths, beads, particles, gels (including aerogels), capsules, and coatings. In one embodiment, the flavorant-infused material comprises a liquid solution or emulsion comprising a liquid carrier and a flavorant admixed with the liquid carrier, and an aerosol jet array is positioned within the second aerosol delivery pathway to form droplets from the flavorant-infused material.

The housing can include a plurality of different flavorant-infused materials, each flavorant-infused material positioned within a separate aerosol delivery pathway and in fluid communication with a separate air inlet. In certain embodiments, the device can further include a mouth-end cap having first and second apertures, the first aperture downstream from, and in fluid communication with, the first aerosol delivery pathway and the second aperture downstream from, and in fluid communication with, at least one of the separate aerosol delivery pathways having a flavorant-infused material positioned therein. The mouth-end cap is optionally rotatable such that a user can move the second aperture into fluid communication with different aerosol delivery pathways having a flavorant-infused material positioned therein.

The atomizer can be located within a separate housing upstream from the housing providing multiple aerosol pathways, the housing providing multiple aerosol pathways being fixedly or removably attached to the separate housing. Alternatively, the atomizer is located within the housing providing multiple aerosol pathways. The first aerosol delivery pathway and the second aerosol delivery pathway can be in a side-by-side configuration within the housing.

In certain embodiments, the first aerosol delivery pathway is centrally located within the housing and the second aerosol delivery pathway is an annular region surrounding the first aerosol delivery pathway. For example, the annular region surrounding the first aerosol delivery pathway can be divided into a plurality of separate aerosol delivery pathways, each containing a different flavorant-infused material and in fluid communication with a separate air inlet. The device can further include a mouth-end cap having first and second apertures, the first aperture downstream from, and in fluid communication with, the first aerosol delivery pathway and the second aperture downstream from, and in fluid communication with, at least one of the separate aerosol delivery pathways having a flavorant-infused material positioned therein. Advantageously, the mouth-end cap is rotatable such that a user can move the second aperture into fluid communication with different aerosol delivery pathways having a flavorant-infused material positioned therein.

Still further, at least one breakable capsule containing an internal payload comprising a flavorant can be positioned within the second aerosol delivery pathway.

In one embodiment, the device includes a rotatable absorbent material in fluid communication with a flavorant-infused material comprising a liquid solution or emulsion comprising a liquid carrier and a flavorant admixed with the liquid carrier, the rotatable absorbent material adapted to produce droplets of the flavorant-infused material during rotation.

Additional optional components of the device include one or more of: (a) an electrical power source configured to provide electrical current flow to the heating element or piezoelectric element; (b) a controller adapted for controlling electrical current flow from the electrical power source; and (c) a flow sensor in communication with the controller and adapted to sense a pressure drop within the aerosol delivery device or a portion thereof.

In another aspect, the invention provides a method for delivering multiple aerosols from an aerosol delivery device having at least one mouth-end opening to an oral cavity of a user, comprising: (i) forming a first aerosol by flowing air through an atomizer, the atomizer in fluid communication with an aerosol precursor composition, a first aerosol delivery pathway leading to a mouth-end opening of the aerosol delivery device, and a first air inlet; (ii) forming a second aerosol by flowing air through a second aerosol delivery pathway separate from the first aerosol delivery pathway, the second aerosol delivery pathway containing a flavorant-infused material therein and being in fluid communication with a second air inlet and a mouth-end opening of the aerosol delivery device; and (iii) passing the first and second aerosols through at least one mouth-end opening of the aerosol delivery device into the oral cavity of the user. Advantageously, the liquid aerosol precursor composition is substantially flavorant-free and optionally contains nicotine.

These and other features, aspects, and advantages of the disclosure will be apparent from a reading of the following detailed description together with the accompanying drawings, which are briefly described below.

BRIEF DESCRIPTION OF THE FIGURES

Figure 1:
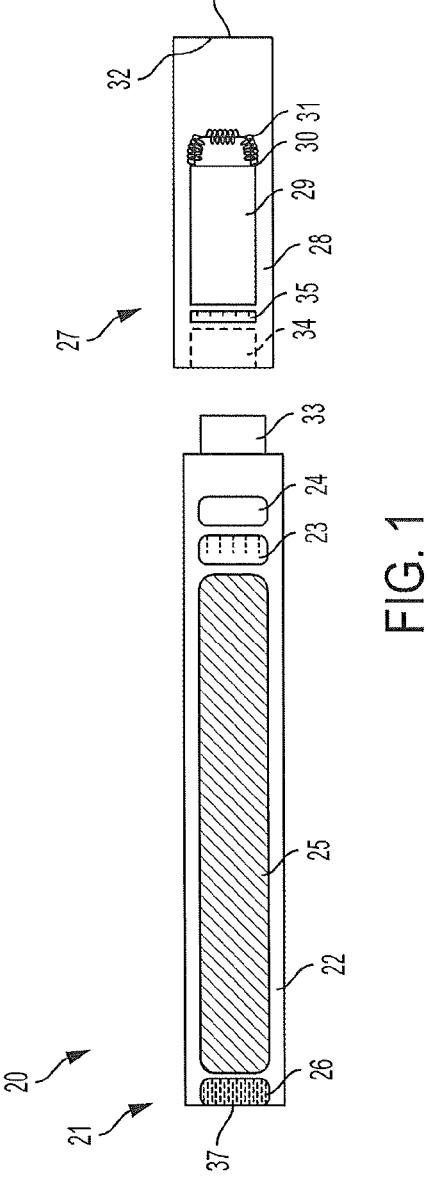
Figure 2:
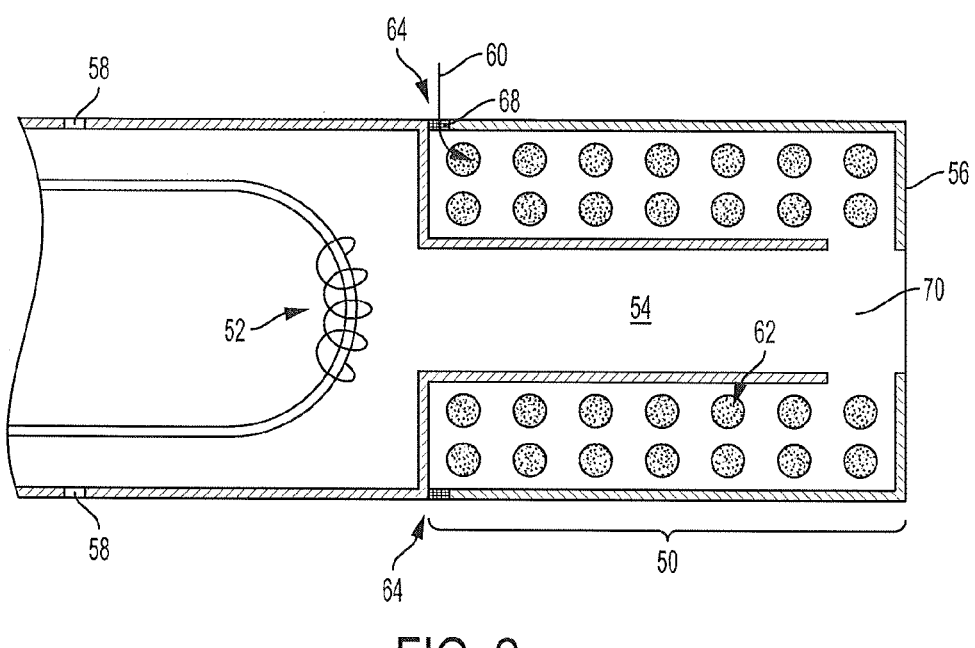
Figure 3:
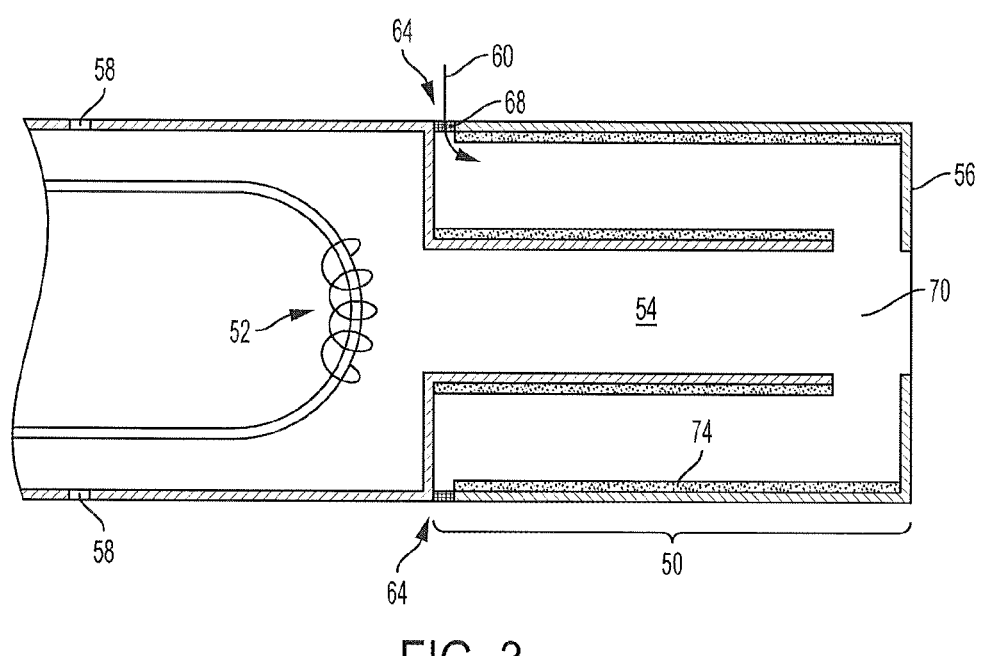
Figure 4:
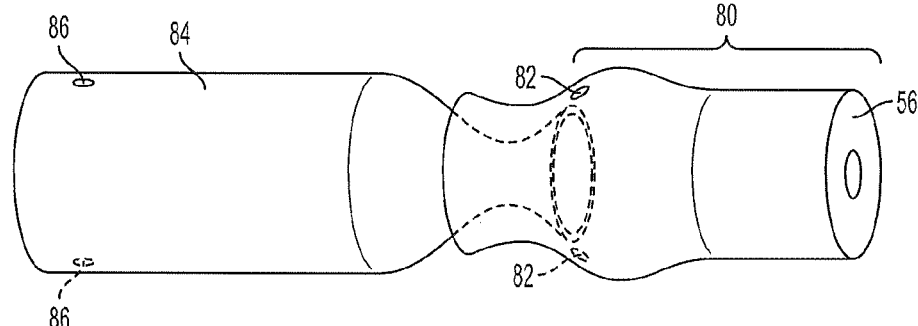
Figure 5:
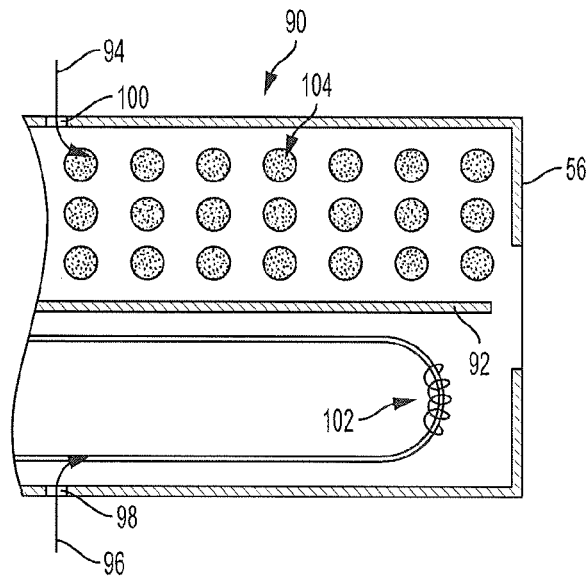
Figure 6:
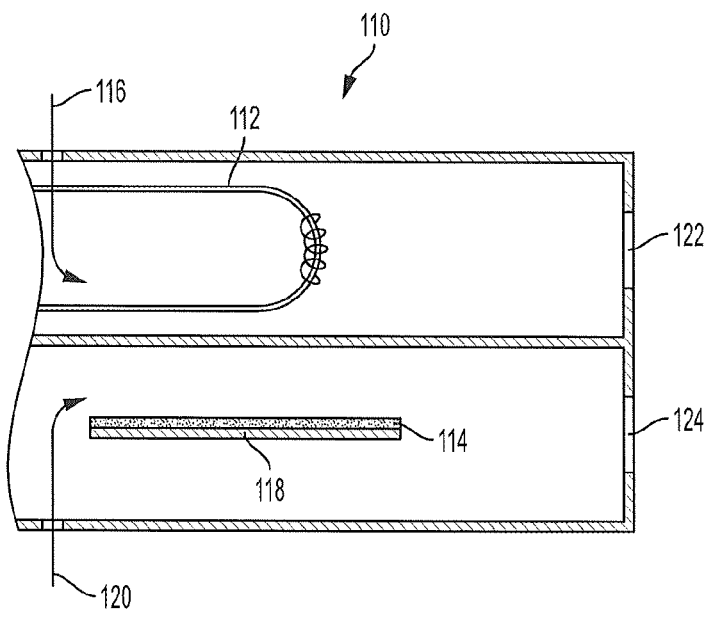
Figure 7:
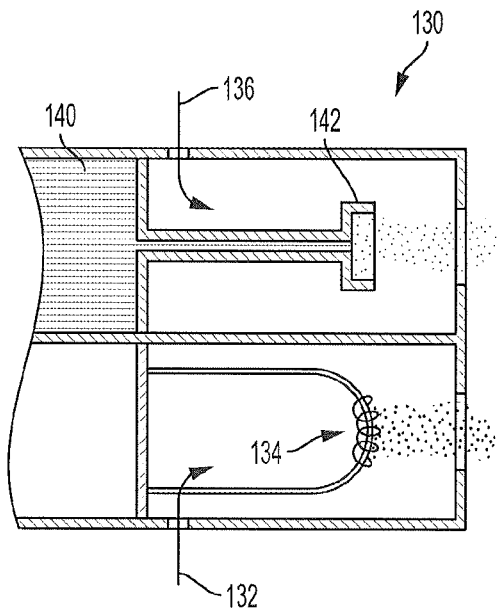
Figure 8:
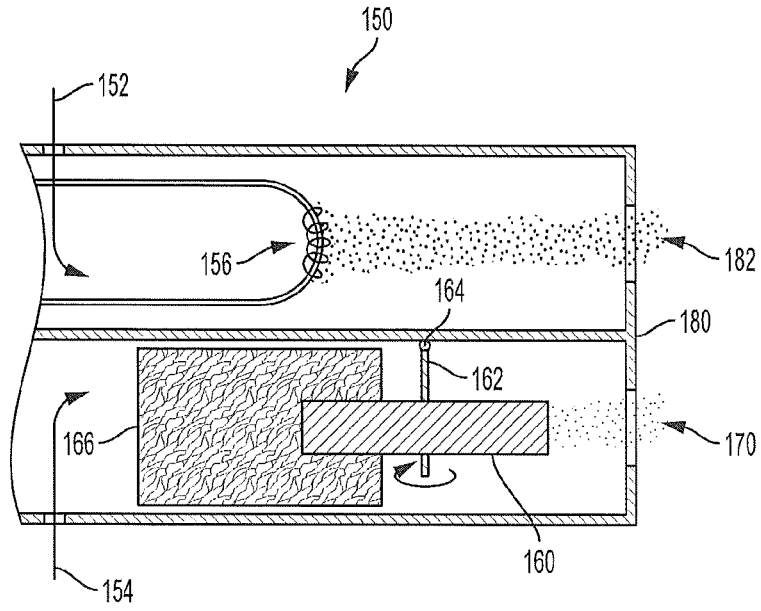
Figure 9:
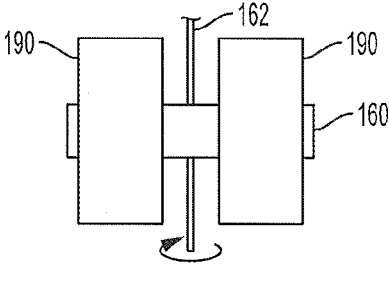
Figure 10:
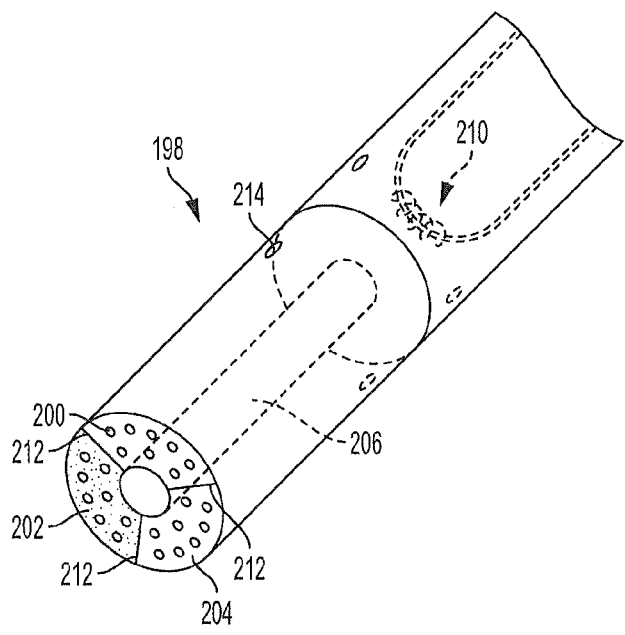
Figure 11:
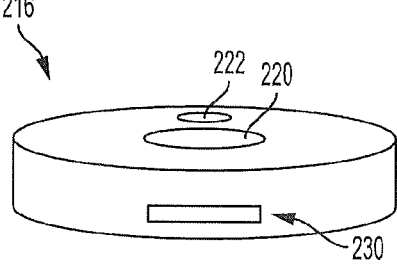

Having thus described the disclosure in the foregoing general terms, reference will now be made to the accompanying drawings, which are not necessarily drawn to scale, and wherein:

FIG. 1 illustrates an aerosol delivery device comprising a cartridge and a control body in an assembled configuration according to an example embodiment of the present disclosure;

FIG. 2 illustrates a cross-sectional view of a first embodiment of a housing containing multiple aerosol flow paths for generation and transport of two separate aerosols;

FIG. 3 illustrates a cross-sectional view of a second embodiment of a housing containing multiple aerosol flow paths for generation and transport of two separate aerosols;

FIG. 4 illustrates a perspective view of a housing with multiple aerosol delivery pathways removably attached to the mouth-end of an aerosol delivery device;

FIG. 5 illustrates a cross-sectional view of a housing with multiple aerosol flow paths according to another embodiment of the present disclosure;

FIG. 6 illustrates a cross-sectional view of a housing with multiple aerosol flow paths according to yet another embodiment of the present disclosure;

FIG. 7 illustrates a cross-sectional view of a housing with multiple aerosol flow paths according to a still further embodiment of the present disclosure;

FIG. 8 illustrates a cross-sectional view of a housing with multiple aerosol flow paths according to an additional embodiment of the present disclosure;

FIG. 9 illustrates the presence of blocking plates downstream from the rotatable adsorbent material of FIG. 8 according to an embodiment of the present disclosure;

FIG. 10 illustrates a cutaway perspective view of a housing with multiple aerosol flow pathways according to an additional embodiment of the present disclosure; and FIG. 11 illustrates a perspective view of a mouth-end cap with multiple openings for use with a housing with multiple aerosol flow paths according to the embodiment of FIG. 10.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The invention provides an aerosol delivery device that includes a reservoir containing a liquid aerosol precursor composition and an atomizer. The atomizer is configured to produce a first aerosol that can be delivered to the oral cavity of a user of the device. In certain advantageous embodiments, the liquid precursor composition can be substantially flavorant-free so that flavorant compounds are not subjected to conditions within the atomizer that may lead to decomposition or other chemical modification of the flavorant, which could potentially cause deleterious impact on the aerosol delivered by the device, such as negative sensory impact. As used herein, "substantially flavorant-free" refers to a liquid aerosol precursor composition having less than about 0.1 percent by weight flavorant component(s), more typically less than about 0.05 percent by weight or less than about 0.01 percent by weight (or flavorant-free compositions), based on overall weight of the precursor composition.

The aerosol precursor composition can vary. Typically, the aerosol precursor composition is comprised of a combination or mixture of various ingredients or components. The selection of the particular aerosol precursor components, and the relative amounts of those components used, may be altered in order to control the overall chemical composition of the mainstream aerosol produced by the device. For example, representative generally liquid aerosol precursor compositions may have the form of liquid solutions, viscous gels, mixtures of miscible components, or liquids incorporating suspended or dispersed components. Typical aerosol precursor compositions are capable of being vaporized upon exposure to heat under those conditions that are experienced during use of the aerosol generation arrangement(s) that are characteristic of the present disclosure; and hence are capable of yielding vapors and aerosols that are capable of being inhaled.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

As noted above, highly purified tobacco-derived nicotine (e.g., pharmaceutical grade nicotine having a purity of greater than 98% or greater than 99%) or a derivative thereof can be used in the present invention. Representative nicotine-containing extracts can be provided using the techniques set forth in U.S. Pat. No. 5,159,942 to Brinkley et al., which is incorporated herein by reference. In certain embodiments, the products of the invention can include nicotine in any form from any source, whether tobacco-derived or synthetically-derived. Nicotinic compounds used in the products of the invention can include nicotine in free base form, salt form, as a complex, or as a solvate. See, for example, the discussion of nicotine in free base form in U.S. Pat. App. Pub. No. 2004/0191322 to Hansson, which is incorporated herein by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12, 43-54 (1983). Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate), chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotinic compound is in the form of a salt with an organic acid moiety, including, but not limited to, levulinic acid as discussed in U.S. Pat. App. Pub. No. 2011/0268809 to Brinkley et al., which are incorporated herein by reference.

The aerosol precursor composition may also incorporate so-called "aerosol forming materials." Such materials may, in some instances, have the ability to yield visible (or not visible) aerosols when vaporized upon exposure to heat under those conditions experienced during normal use of aerosol generation arrangement(s) that are characteristic of the present disclosure. Such aerosol forming materials include various polyols or polyhydric alcohols (e.g., glycerin, propylene glycol, and mixtures thereof). Aspects of the present disclosure also incorporate aerosol precursor components that can be characterized as water, saline, moisture or aqueous liquid. During conditions of normal use of certain aerosol generation arrangement(s), the water incorporated within those aerosol generation arrangement(s) can vaporize to yield a component of the generated aerosol. As such, for purposes of the current disclosure, water that is present within the aerosol precursor composition may be considered to be an aerosol forming material.

Aerosol precursor compositions also may include ingredients that exhibit acidic or basic characteristics (e.g., organic acids, ammonium salts or organic amines). For example, certain organic acids (e.g., levulinic acid, succinic acid, lactic acid, and pyruvic acid) may be included in an aerosol precursor formulation incorporating nicotine, preferably in amounts up to being equimolar (based on total organic acid content) with the nicotine. For example, the aerosol precursor may include about 0.1 to about 0.5 moles of levulinic acid per one mole of nicotine, about 0.1 to about 0.5 moles of succinic acid per one mole of nicotine, about 0.1 to about 0.5 moles of lactic acid per one mole of nicotine, about 0.1 to about 0.5 moles of pyruvic acid per one mole of nicotine, or various permutations and combinations thereof, up to a concentration wherein the total amount of organic acid present is equimolar to the total amount of nicotine present in the aerosol precursor composition. However, in some aspects of the present disclosure, the aerosol precursor composition is free of any acidic (or basic) characteristics or additives.

As one non-limiting example, a representative aerosol precursor composition or substance can include glycerin, propylene glycol, water, saline, and nicotine, and combinations or mixtures of any or all of those components. For example, in one instance, a representative aerosol precursor composition may include (on a weight basis) about 70% to about 100% glycerin, and often about 80% to about 90% glycerin; about 5% to about 25% water, often about 10% to about 20% water; and about 0.1% to about 5% nicotine, often about 2% to about 3% nicotine. In one particular non-limiting example, a representative aerosol precursor composition may include about 84% glycerin, about 14% water, and about 2% nicotine. The representative aerosol precursor composition may also include propylene glycol, optional flavoring agents or other additives in varying amounts on a weight basis. In some instances, the aerosol precursor composition may comprise up to about 100% by weight of any of glycerin, water, and saline, as necessary or desired.

Representative types of aerosol precursor components and formulations are also set forth and characterized in U.S. Pat. No. 7,726,320 to Robinson et al., U.S. Pat. No. 8,881, 737 to Collett et al., and U.S. Pat. No. 9,254,002 to Chong et al.; and U.S. Pat. App. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery device is such that the device provides acceptable sensory and desirable performance characteristics. For example, it is highly preferred that sufficient amounts of aerosol forming material (e.g., glycerin and/or propylene glycol), be employed in order to provide for the generation of a mainstream aerosol (visible or not visible) that in many regards resembles the appearance of tobacco smoke. The amount of the aerosol precursor composition within the device may be dependent upon factors such as the number of puffs desired from the device. Typically, the amount of the aerosol precursor composition incorporated within the aerosol delivery device is less than about 2 g, generally less than about 1.5 g, often less than about 1 g and frequently less than about 0.5 g.

The aerosol delivery devices of the invention typically provide a separate aerosol delivery pathway for any flavorant components included in the device. The separate aerosol delivery pathway is typically defined by a housing that includes one or more wall structures within the housing that create separate pathways for the first aerosol from the atomizer and a second aerosol that includes one or more flavorant components. The wall structures that separate the aerosol pathways are typically non-porous to aerosol, meaning the walls can be solid structures that do not allow transport of aerosol therethrough. However, in certain embodiments, the wall structure may exhibit some level of permeability or porosity that merely reduces or retards (without completely blocking) transport of aerosol between the pathways, such as porous ceramic structures, porous glass structures, or fibrous mat materials (e.g., fiberglass).

In certain embodiments of the invention, flavorants are prevented from interacting with the atomizer in a disadvantageous manner. Additionally, in various embodiments of the invention, the use of two aerosol delivery pathways prevents the first aerosol (e.g., the aerosol produced in an atomizer) from passing through a flavorant-infused material where condensation of the aerosol could occur before reaching the mouth-end opening of the device, which can change the nature and character of the aerosol delivered to the user and cause clogging or plugging of the flavorant-infused material.

Typically, each pathway within the housing will be associated with a separate air inlet for drawing air into the device as necessary to form each aerosol. A separate airflow pathway also contributes to keeping flavorant components segregated from the atomizer.

Although several embodiments of the invention relate to devices with two aerosol pathways (i.e., dual pathways), the invention is not limited to devices with only two pathways. Instead, multiple aerosol pathways of varying number could be utilized, particularly where the device is adapted to deliver several different flavorants that are selectable by the user.

As used herein, reference to "flavorant" refers to compounds or components of the device that can be aerosolized and delivered to a user and which impart a sensory experience in terms of taste and/or aroma. Exemplary flavorants include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar and pipe tobaccos. Syrups, such as high fructose corn syrup, also can be employed.

The flavorant is typically utilized in a form that allows volatilization of the flavorant into aerosol or vapor form without significant heating to form the second aerosol, although some heating can be employed as needed. In certain embodiments, the flavorant is used in the form of a flavorant-infused material, which comprise one or more flavorants combined with a liquid carrier to form a solution or emulsion, or which comprise one or more flavorants carried by a substrate. The form of the flavorant-infused material can vary, with examples including porous monoliths, beads, particles, gels, capsules, and coatings. The substrate material can be constructed of, for example, carbon materials, ceramics, polymers, composites, metals, cellulosics (e.g., microcrystalline cellulose), and the like. In certain embodiments, the substrate will either be porous (e.g., a porous carbon material) or in the form of a gel or coating that allows transport of the flavorant to the surface thereof for volatilization. Exemplary coating materials that can be combined with a flavorant to produce a flavor-infused coating include gelatin, waxes, and the like.

In another embodiment, the flavorant-infused material is a polymeric material having a flavorant infused therein. Examples of polymeric material that can be infused with a flavorant include polyolefins (e.g., polyethylene or polypropylene) or ethylene vinyl acetate. Flavorant-infused materials are commercially available from, for example, Scent-Sational Technologies, LLC, MOGO Sport, Addmaster (e.g., Scentmaster Fragrance Technology), Mint-X Corporation, Rotuba (e.g., AUROCELL material), and the like. See, also, U.S. Pat. No. 7,811,587 to Katoh et al., which is incorporated by reference herein. Note that where a flavorant is infused in a plastic or polymeric material, the polymeric material can be produced with a gradient of flavorant concentration in order to enhance flavorant release from a desired surface of the material or the polymer material can include a roughened or porous surface designed to enhance flavorant release.

Representative flavorant-infused materials can include beads or other objects produced from a formulation that incorporates tobacco (e.g., particulate tobacco), components of tobacco and/or materials that are otherwise derived from tobacco. In some embodiments, the beads may include or otherwise comprise or be configured as, for example, marumerized tobacco beads of varying shapes and sizes, a monolith of bonded (e.g., sintered) beads; a porous monolith; a single porous structure; a honeycomb monolith; a single piece of a porous material; beads of extruded tobacco; beads of porous material containing tobacco extract (e.g., calcium carbonate, ceramic, or the like); reconstituted tobacco shreds; expanded tobacco shreds; extruded rods of various materials (including hollow cylinders and slotted rods) containing tobacco flavors; shavings, granules, capsules, and/or microcapsules of various materials containing tobacco flavors or other substances, whether in a liquid or other form; and treatments or combinations thereof.

As noted above, the flavorant-infused material could be in the form of a capsule, such as a breakable capsule containing a frangible shell and an internal payload including the flavorant. Any of the illustrated embodiments could include one or more breakable capsules within a housing that is sufficiently pliable to allow the user to squeeze the device and break the capsule to release the flavorant. Numerous ways of handling breakable capsules and incorporating those breakable capsules into components of smoking articles and vapor delivery systems have been proposed. For example, various types of capsules suitable for use in smoking articles, smoking article components that incorporate breakable capsules, and equipment and techniques associated with manufacturing those smoking article components, are proposed in U.S. Pat. No. 7,479,098 to Thomas et al.; U.S. Pat. No. 7,833,146 to Deal; U.S. Pat. No. 7,984,719 to Dube et al.; U.S. Pat. No. 7,972,254 to Stokes et al.; U.S. Pat. No. 8,186,359 to Ademe et al.; U.S. Pat. No. 8,262,550 to Barnes et al.; U.S. Pat. No. 8,353,810 to Garthaffner et al.; U.S. Pat. No. 8,381,947 to Garthaffner et al.; U.S. Pat. No. 8,459,272 to Karles et al.; U.S. Pat. No. 8,739,802 to Fagg; and U.S. Pat. No. 8,905,243 to Dixon et al.; and U.S. Pat. App. Pub. Nos. 2010/0184576 to Prestia et al.; 2011/0053745 to Iliev et al.; 2011/0271968 to Carpenter et al.; 2012/0245007 to Henley et al. and 2013/0085052 to Novak III, et al.; which are incorporated herein by reference. Additionally, representative cigarette products that possess filter elements incorporating breakable capsules have been marketed throughout the world under the brand names such as "Marlboro W-Burst 5," "Kent iSwitch," "Kool Boost," "Camel Lights with Menthol Boost," "Camel Crush," "Camel Silver Menthol," "Camel Filters Menthol," and "Camel Crush Bold." Furthermore, representative types of vapor delivery systems that incorporate breakable capsules have been proposed in U.S. Pat. App. Pub. Nos. 2014/0261486 to Potter, 2015/0059780 to Davis; and 2015/0335070 to Sears et al.; which are incorporated herein by reference.

Exemplary types of capsules, capsule ingredients, capsule configurations and formats, capsule sizes, capsule properties and capsule preparation techniques are set forth in U.S. Pat. No. 7,984,719 to Dube et al.; U.S. Pat. No. 8,470,215 to Zhang and U.S. Pat. No. 8,695,609 to Dube; U.S. Pat. App. Pub. No. 2014/0053855 to Hartmann et al.; and PCT WO 03/009711 to Kim and PCT WO 2014/170947 to Iwatani; which are incorporated herein by reference. Additionally, examples of representative types of capsules that have been commercially available are set forth in U.S. Pat. No. 8,695,609 to Dube; which is incorporated herein by reference.

In general, as used herein, the term "beads" is meant to include beads, pellets, or other discrete small units or pieces of that may include (in addition to those otherwise disclosed herein), for example, carbon pieces, extruded carbon pieces cut into pellets, ceramic beads, marumerized or spheronized tobacco pieces, and the like, or combinations thereof. For example, granules, pellets or beads can be generally cylindrical or spherical extruded or compressed granules, pellets or beads comprised of a moistened mixture or slurry of milled tobacco lamina, fillers (e.g., granular calcium carbonate), flavors, visible aerosol forming materials and binders (e.g., carboxy methylcellulose) that are formed, cut or spun to the desired size and shape, and then dried to retain the desired configuration. However, such "pellets" or "beads" may comprise any suitable elements, or combination of elements, meeting the preferred aspects as disclosed herein. For example, some or all of the beads or pellets can comprise spherical capsules that are heat sensitive, so that when included in the aerosol-generating element and exposed to heat, the rupture or decomposition thereof causes the release of glycerin, propylene glycol, water, saline, tobacco flavor and/or nicotine or other substances or additives. Also, the beads can comprise ceramic or absorbent clay or silica or absorbent carbon to hold and release an aerosol former. Further, in some aspects, the beads/pellets may comprise a heat conductive material such as, for example, heat conductive graphite, heat conductive ceramic, a metal, tobacco cast on foil, a metal or other suitable material impregnated with appropriate aerosol-generating substances such as glycerin and flavor(s), or a suitable cast sheet material appropriately formed into the desired beads/pellets.

In one particular example, the beads/pellets (particles) may be comprised, by weight, of between about 15% and about 60% of finely milled tobacco particles (e.g., a blend of Oriental, burley and flue-cured tobaccos, essentially all Oriental tobacco, essentially all burley tobacco, or essentially all flue-cured tobacco), between about 15% and about 60% of finely milled particles of calcium carbonate (or finely milled clay or ceramic particles), between about 10% and about 50% of glycerol (and optionally a minor amount of flavors), between about 0.25% and about 15% of a binder (preferably carboxymethylcellulose, guar gum, potassium, or ammonium alginate), and between about 15% and about 50% of water. In another example, the beads/pellets (particles) may be comprised of about 30% of finely milled tobacco particles (e.g., a blend of Oriental, burley and flue-cured tobaccos, essentially all Oriental tobacco, essentially all burley tobacco, or essentially all flue-cured tobacco), about 30% of finely milled particles of calcium carbonate (or finely milled clay or ceramic particles), about 15% of glycerol (and optionally a minor amount of flavors), about 1% of a binder (preferably carboxymethylcellulose, guar gum, potassium, or ammonium alginate), and about 25% of water. In such examples, the particles may be compressed to hold the glycerol and, upon compression, may form a porous matrix that facilitates migration of the aerosol generating components to promote efficient aerosol formation. The manner by which the aerosol forming material is contacted with the substrate material can vary. The aerosol forming material can be applied to a formed material, can be incorporated into processed materials during manufacture of those materials, or can be endogenous to that material. Aerosol-forming material, such as glycerin, can be dissolved or dispersed in an aqueous liquid, or other suitable solvent or liquid carrier, and sprayed onto that substrate material. See, for example, U.S. Pat. App. Pub. No. 2005/0066986 to Nestor et al. and 2012/0067360 to Conner et al.; which are incorporated herein by reference. The calcium carbonate or other inorganic filler assists in creating porosity within the particles, and may also function to absorb heat which may, in some instances limit or otherwise prevent scorching of the aerosol generating components, as well as assisting in and promoting aerosol formation. See also, for example, those types of materials set forth in U.S. Pat. No. 5,105,831 to Banerjee, et al., and U.S. Pat. App. Pub. Nos. 2004/0173229 to Crooks et al.; 2011/0271971 to Conner et al.; and 2012/0042885 to Stone et al.; which are incorporated herein by reference.

In one embodiment, the flavorant-infused materials, such as those in the form of beads or pellets, can be smoke-treated to impart smoky flavor or aroma. For example, the beads or pellets can be prepared and then subjected to smoke from a combustible source, such as a wood source (e.g., wood selected from hickory, maple, oak, apply, cherry, or mesquite). The beads or pellets can be treated with the smoke for a time sufficient to impart the desired smoky flavor or aroma, with an exemplary time range being about 5 to about 45 minutes. The manner in which the beads or pellets are contacted with smoke can vary, with one example involving heating wood chips in a container until smoke is produced (e.g., heating wood chips to a temperature of about 350-400° F.) and placing the beads or pellets to be treated within a closed environment with the smoke produced by the wood chips.

In some aspects, the beads/pellets of flavorant-infused material may originate from a tobacco material cast on a foil/paper laminate. More particularly, the tobacco material may comprise, for example, a slurry including reconstituted tobacco, glycerin, and a binder material. Such a tobacco material is disclosed, for example, in U.S. Pat. No. 5,101,839 to Jakob et al. and U.S. Pat. App. Pub. No. 2010/0186757 to Crooks et al., which are incorporated herein by reference. In addition, the slurry can incorporate granular inorganic material (i.e., calcium carbonate). The slurry is cast unto a paper element of a foil-paper laminate, such as disclosed, for example, in U.S. Pat. No. 8,678,013 to Crooks et al. and U.S. Pat. No. 7,647,932 to Cantrell et al., which is also incorporated herein by reference, and the assembled cast sheet product is then dried, for instance by the application of heat (i.e., by heated air, microwave drying, etc.). The paper element may have, for instance, a particular porosity or texture to promote an intimate contact and interaction with the slurry, for instance, over direct contact between the slurry and the foil. However, the exemplary aspect presented herein does not preclude casting the tobacco material (i.e., slurry) directly on a metal foil or other suitable thin film heat conductor. Once such a laminate is cast, the dried cast sheet (i.e., the foil/paper/tobacco material) may be shredded, diced, or otherwise separated into a plurality of cast sheet portion elements, wherein each such element preferably includes a portion of the tobacco material (i.e., the substrate) intimately interacted with a portion of the paper element which, in turn, is in intimate contact with a portion of the foil element of the foil-paper laminate. Further examples of flavorant-infused materials can be found, for example, in U.S. Pat. App. Pub. No. 2016/0073695 to Sears et al., which is incorporated by reference herein.

The aerosol precursor composition forming the first aerosol and the composition of the flavorant-infused material forming the second aerosol are advantageously selected so as to complement one another to produce a desirable sensory experience. In certain embodiments, for example, the nicotine content of the aerosol precursor composition and the flavorant-infused material are selected such that either or both of the aerosol precursor composition and the flavorant-infused material may contain nicotine or a nicotinic compound or may be viewed as substantially or completely free of nicotine or a nicotinic compound. In other words, all nicotine content can be within the flavorant-infused material or all nicotine content can be in the aerosol precursor composition or both compositions can include nicotine in some form.

In addition, the first and second aerosols can be configured such that the first aerosol produced by the atomizer is respirable and the second aerosol comprising the flavorant is non-respirable. As used herein, "respirable" refers to an aerosol that produces particles of a size sufficiently small to penetrate beyond terminal bronchioles in the lung and enter the gas exchange region. Respirable particles are typically less than about 10 μm in terms of aerodynamic diameter. As used herein, "non-respirable" particles are those that can be inhaled into the mouth, but which cannot penetrate into the gas exchange region of the lungs. Non-respirable particles are typically between about 10 μm and about 100 μm in terms of aerodynamic diameter. In this manner, the first aerosol can deliver components that are beneficially delivered into the lungs while the flavorant-infused material can deliver flavorants that only enter the oral cavity and or the throat of the user in order to impart the desired sensory characteristics.

The present disclosure provides descriptions of aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized in certain embodiments as an electronic smoking article such as an electronic cigarette or "e-cigarette."

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, aerosols, and combinations thereof of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

The invention will now be described by reference to various figures. Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition as otherwise discussed herein (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined air flow path through the article such that aerosol generated can be withdrawn therefrom upon draw). Alternatively, an aerosol delivery device of the invention can utilize a piezoelectric element to form the first aerosol instead of a heating element as disclosed herein. See, for example, the piezoelectric element set forth in U.S. Pat. App. Pub. Nos. 2006/0196518 to Hon; 2013/0319404 to Feriani et al.; and 2016/0366946 to Murison et al., each of which is incorporated by reference herein.

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently lightweight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™ COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™ JET™, MAXXQ™, PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC;

RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; AVIGO, VUSE, VUSE CONNECT, VUSE FOB, VUSE HYBRID, ALTO, ALTO+, MODO, CIRO, FOX+FOG, AND SOLO+ by R. J. Reynolds Vapor Company; MISTIC MENTHOL by Mistic Ecigs; and VYPE by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGON-FLY™; EMIST™; EVERSMOKE™; GAMUCCI®; HYBRID FLAME™; KNIGHT STICKS™; ROYAL BLUES™; SMOKETIP®; SOUTH BEACH SMOKE™ Additional manufacturers, designers, and/or assignees of components and related technologies that may be employed in the aerosol delivery device of the present disclosure include Shenzhen Jieshibo Technology of Shenzhen, China; Shenzhen First Union Technology of Shenzhen City, China; Safe Cig of Los Angeles, CA; Janty Asia Company of the Philippines; Joyetech Changzhou Electronics of Shenzhen, China; SIS Resources; B2B International Holdings of Dover, DE; Evolv LLC of OH; Montrade of Bologna, Italy; Shenzhen Bauway Technology of Shenzhen, China; Global Vapor Trademarks Inc. of Pompano Beach, FL; Vapor Corp. of Fort Lauderdale, FL; Nemtra GMBH of Raschau-Markersbach, Germany, Perrigo L. Co. of Allegan, MI; Needs Co., Ltd.; Smokefree Innotec of Las Vegas, NV; McNeil AB of Helsingborg, Sweden; Chong Corp; Alexza Pharmaceuticals of Mountain View, CA; BLEC, LLC of Charlotte, NC; Gaitrend Sarl of Rohrbach-les-Bitche, France; FeelLife Bioscience International of Shenzhen, China; Vishay Electronic BMGH of Selb, Germany; Shenzhen Smaco Technology Ltd. of Shenzhen, China; Vapor Systems International of Boca Raton, FL; Exonoid Medical Devices of Israel; Shenzhen Nowotech Electronic of Shenzhen, China; Minilogic Device Corporation of Hong Kong, China; Shenzhen Kontle Electronics of Shenzhen, China, and Fuma International, LLC of Medina, OH, 21st Century Smoke of Beloit, WI, and Kimree Holdings (HK) Co. Limited of Hong Kong, China.

One example embodiment of a typical aerosol delivery device, i.e., electronic cigarette, 20 is provided in FIG. 1. An electronic cigarette 20 includes a first end 36, which is the mouthpiece for the consumer to draw on, and a second end 37, which optionally includes an Light-Emitting Diode (LED) 26. As illustrated therein, a control body 21 can be formed of a control body shell 22 that can include, for example, a control component 23, a flow sensor 24, a battery 25, and an LED 26. A cartridge 27 can be formed of a cartridge shell 28 enclosing the reservoir housing 29 that is in fluid communication with a liquid transport element 30 adapted to wick or otherwise transport an aerosol precursor composition stored in the reservoir housing to a heater 31. An opening 32 may be present in the cartridge shell 28 to allow for egress of formed aerosol from the cartridge 27. Such components are representative of the components that may be present in a cartridge and are not intended to limit the scope of cartridge components that are encompassed by the present disclosure. The cartridge 27 may be adapted to engage the control body 21 through a press-fit engagement between the control body projection 33 and the cartridge receptacle 34. Various other mechanisms may connect the cartridge 27 to the control body 21, such as a threaded engagement, an interference fit, a magnetic engagement, or the like. Such engagement can facilitate a stable connection between the control body 21 and the cartridge 27 as well as establish an electrical connection between the battery 25 and control component 23 in the control body and the heater 31 in the cartridge. The cartridge 27 also may include one or more electronic components 35, which may include an Integrated Circuit (IC), a memory component, a sensor, or the like. The electronic component 35 may be adapted to communicate with the control component 23. For examples of additional aerosol delivery devices see, U.S. Patent Application Publication No. 2015/0144145 to Chang; and U.S. Pat. No. 8,881,737 to Collett, which are hereby incorporated by reference in their entireties.

In specific embodiments, one or both of the cartridge 27 and the control body 21 may be referred to as being disposable or as being reusable. For example, the control body 21 may have a replaceable battery or a rechargeable battery and/or capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 27 may comprise a single-use cartridge, as disclosed in U.S. Pat. No. 8,910,639 to Chang et al., which is incorporated herein by reference in its entirety.

Examples of electrical power sources are described in U.S. Pat. App. Pub. No. 2010/0028766 by Peckerar et al., the disclosure of which is incorporated herein by reference in its entirety. With respect to the flow sensor 24, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. App. Pub. No. 2014/0270727 to Ampolini et al., which is incorporated herein by reference in its entirety.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat.

No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; U.S. Pat. App. Pub. No. 2014/0096781 to Sears et al.; U.S. Pat. App. Pub. No. 2014/0261495 to Novak et al.; U.S. Pat. App. Pub. No. 2015/0335071 to Brinkley et al.; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

The liquid transport element 30 particularly can be a wick that utilizes capillary action in the transport of liquids. A wick for use according to the invention thus can be any material that provides sufficient wicking action to transport one or more components of the aerosol precursor composition to the aerosolization zone. Non-limiting examples include natural and synthetic fibers, such as cotton, cellulose, polyesters, polyamides, polylactic acids, glass fibers, combinations thereof, and the like. Other exemplary materials that can be used in wicks include metals, ceramics, and carbonized materials (e.g., a foam or monolith formed of a carbonaceous material that has undergone calcining to drive off non-carbon components of the material). Wicks further can be coated with materials that alter the capillary action of the fibers, and the fibers used in forming wicks can have specific cross-sectional shape and can be grooved so as to alter the capillary action of the fibers. For example, temperature adaptive polymers can be used. Such adaptive polymers can be coated on fibers or used in other manners, and these polymers are effective for providing altered liquid transport characteristics based on the surrounding conditions. Temperature adaptive polymers particularly can exhibit low transport at reduced temperatures and can exhibit increased transport at increased temperatures. One example is a material known as Adaptive by HeiQ®. Fibers used in forming wicks can be provided singly, bundled, as a woven fabric (including meshes and braids), or as a non-woven fabric. Porosity of the wick material also can be controlled to alter the capillary action of the wick, including controlling average pore size and total porosity. Separate wicks also can have different lengths. The term "wick" is also intended to encompass capillary tubes, and any combination of elements providing the desired capillary action can be used.

Additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety. An example embodiment of a carbon-based cartridge is provided in U.S. Pat. App. Pub. No. 2013/0255702 to Griffith Jr. et al., which is incorporated herein by reference in its entirety.

The remaining figures describe embodiments of housings that provide multiple aerosol delivery pathways as provided by the invention. Some of these housing designs can be implemented as downstream housings fixedly or removably attached to a cartridge of the type shown in FIG. 1. Alternatively, some of the housing embodiments illustrated herein can serve as a replacement for the cartridge component of FIG. 1. Note that, for the sake of brevity, the following housing embodiments are not shown in exhaustive detail but rather focus on the specific aspects associated with the multiple aerosol delivery pathways provided by the invention. Accordingly, it should be understood that the housing embodiments described hereinbelow can include any of the cartridge components noted in FIG. 1 or otherwise disclosed herein.

The embodiment of FIG. 2 is a cross-sectional view of a housing 50 that can serve as an extension at the mouth-end of an aerosol delivery device, such as an extension fixedly or removably attached to the cartridge 27 of FIG. 1. As shown, the housing 50 is positioned downstream from a conventional atomizer 52, which can be, for example, an atomizer as described in reference to FIG. 1, which produces a first aerosol from an aerosol precursor composition as described herein. The first aerosol travels through a central passage 54 within the housing 50 defined by walls within the housing to an opening in the mouth-end cap 56. The cross-sectional shape of the central passage 54 is not intended to be limiting and can be, for example, round, oval, rectangular, and the like. One or more air inlets 58 provide air to the atomizer 52 for formation of the first aerosol. The housing 50 provides a second aerosol delivery pathway 60 through an annular space defined in the housing containing a flavorant-infused material such as a bed of flavor beads or particles 62. The housing 50 includes one or more second air inlets 64 that allow ambient air to enter the housing, interact with the bed of flavor beads or particles 62 and produce a second aerosol, which is also delivered to the opening in the mouth-end cap 56. Optionally, a screen or mesh 68 can be placed in the air inlet 64 to retain the flavor beads or particles 62 within the annular chamber and to regulate the amount of air allowed to enter the housing. As shown, the housing 50 can provide an optional mixing space 70 for the first and second aerosols to mix before exiting the housing through the opening in the mouth-end cap 56.

FIG. 3 shows an alternative embodiment of FIG. 2 wherein the flavorant-infused material is in the form of a coating 74 on internal walls within the housing 50 rather than beads or particles. Without departing from the invention, it is noted that more than one flavorant can be delivered by the embodiment of either FIG. 2 or FIG. 3 through use combinations of beads or particles with different flavorants infused therein or through use of coating materials with different flavorants infused therein. For example, in the embodiment of FIG. 3, the annular space containing the flavorant-infused material could include a first coating material containing a first flavorant on one fraction of the circumference of the housing 50, a second coating material containing a second flavorant on a second fraction of the circumference of the housing, and so on. The walls upon which the coating 74 is placed can be roughened or texturized to increase the surface area for flavorant transfer into aerosol form.

As indicated above, the housing containing the multiple aerosol pathways can be removably attached to the mouth-end of an aerosol delivery device, such as a device as described in FIG. 1. Such an embodiment is shown in FIG. 4, wherein a removable housing 80 having air inlets 82 is connected to the mouth-end of aerosol delivery device 84 having air inlets 86. The internal design of the removable housing 80 can be any of embodiments set forth herein, such as the embodiments illustrated in FIGS. 2 and 3. The connection between the housing 80 and the aerosol delivery device 84 can be formed using various techniques known in the art, such as friction fit, press fit, snap fit, threaded engagement, magnetic engagement, adhesive, and the like.

The two aerosol delivery pathways can be separated using an internal wall that separates the two pathways in a side-by-side arrangement rather than a radially separated design as set forth in FIGS. 2 and 3. For example, as illustrated in FIG. 5, a housing 90 can include an internal wall 92 (which can be impermeable or semi-permeable to aerosol) separating a first aerosol pathway 94 from a second aerosol pathway 96. Separate air inlets 98, 100 are used to allow air to enter the housing 90, each aerosol pathway 94, 96 being associated with at least one air inlet. One pathway can produce an aerosol using an atomizer 102 as described herein and one pathway can produce an aerosol using a flavorant-infused material 104 as described herein. In the embodiment of FIG. 5, similar to FIGS. 2 and 3, both generated aerosols are delivered though the same opening in a mouth-end cap 56.

In a further embodiment shown in in FIG. 6, a housing 110 can include two parallel aerosol delivery pathways that delivery aerosols using different heating techniques. One aerosol delivery pathway 116 includes an atomizer 112. The other aerosol delivery pathway 120 includes a flavorant-infused material 114 in close proximity to a heater 118. The heater 118 can vary in design, and can include, for example, a flat plate configuration, a coil heater, a needle or blade heater, and the like. The flavorant-infused material 114 can be operatively positioned adjacent or otherwise proximal to (e.g., surrounding) the heater 118. Alternatively the flavorant-infused material 114 can be downstream from the heater 118 such that the heater pre-heats air entering the housing 110 prior to contact with the flavorant-infused material. The flavorant-infused material 114 can take a variety of forms, such as a sol-gel material containing flavorant adhered to the heater 118, a flavorant-infused coating coated on the heater, a solid or gel flavorant-infused material packed in the chamber around the heater, and the like. A flavorant-infused liquid could also be sprayed on the heater 118, which can exhibit a roughened or porous surface to hold the liquid on the heater. Both heaters can be operatively connected to a power source and controller as discussed in connection with FIG. 1. In the illustrated embodiment, the two aerosol pathways 116, 120 can exit the mouth-end of the housing 110 through separate openings 122, 124. Note that a heater could be incorporated into the aerosol delivery pathway comprising the flavorant-infused material in other illustrated embodiments as well, such as the embodiments of FIGS. 2 and 3.

In another embodiment shown in in FIG. 7, a housing 130 can include two parallel aerosol delivery pathways that delivery aerosols using different techniques. One aerosol delivery pathway 132 includes an atomizer 134. The other aerosol delivery pathway 136 includes a flavorant-infused liquid 140 in fluid communication with a print head 142 (i.e., an aerosol jet array), such as a bubble-jet, piezo-activated jet, or other aerosol-forming print head device. Both aerosol-forming devices can be operatively connected to a power source and controller as discussed in connection with FIG. 1. Examples of print heat aerosol forming devices are set forth, for example, in U.S. Pat. App. Pub. No. 2015/0114409 to Brammer et al., which is incorporated by reference herein in its entirety. A print head 142 is particularly useful for producing an aerosol that is non-respirable. In this manner, the aerosol produced in the aerosol delivery pathway 136 remains in the oral cavity and throat region and provides a desirable sensory experience to the user. The aerosol produced in the aerosol delivery pathway 132 can be adapted to produce respirable particles that enter the lungs of the user.

In yet another embodiment illustrated in FIG. 8, a housing 150 provides two aerosol delivery pathways 152, 154, including a first pathway 152 that includes an atomizer 156 adapted to produce a first aerosol 182 as described herein and a second pathway 154 that includes a rotating absorbent material 160 (e.g., a cylindrically shaped sponge-like material) positioned on an axle 162 that is connected to a small electric motor 164. A substrate 166 containing flavorant-infused material in liquid form is in fluid communication with the rotating absorbent material 160 such that flavorant-infused material can be transferred to the rotating absorbent material. The rotating absorbent material 160 spins, causing aerosol droplets 170 to form and then exit the mouth-end 180 of the device due to centrifugal force. The two aerosols, 170, 182 can combine in the oral cavity of the user. The aerosol droplets 170 produced in this manner will tend to be non-respirable while the aerosol 170 produced in the atomizer 156 is typically respirable. Both aerosol-forming devices can be operatively connected to a power source and controller as discussed in connection with FIG. 1. The electric motor 164 can be activated by a flow sensor as set forth herein or activation of the rotatable adsorbent material 160 can be accomplished without an electric motor by incorporating a mechanical device such as a lever or wheel that can be manipulated by the user (not shown).

FIG. 9 illustrates a view, facing upstream into the device, of the rotatable absorbent material 160 with two blocking plates 190 positioned downstream to catch aerosol droplets 170 that spin off from the rotatable absorbent material in a direction other than toward an opening in the mouth-end of the device. These droplets deposit on the surface of the blocking plates 190 and return either to the rotatable absorbent material 160 or the substrate 166 when the device is positioned such that gravity causes the deposited droplets to move upstream within the device.

FIG. 10 illustrates another embodiment where a housing 198 includes multiple aerosol delivery pathways containing flavorant-infused materials are provided in outer segments, 200, 202, 204, surrounding a central aerosol delivery pathway 206 positioned to deliver an aerosol from an upstream atomizer 210. Each outer segment can contain a different flavorant and can include a separate air inlet 214, and each segment has a porous end such that aerosol generated therein can exit the mouth-end of the device. The outer segments are separated from one another by walls 212, which can be non-porous or semi-permeable.

The embodiment of FIG. 10 can be augmented with a rotatable mouth-end cap 216 set forth in FIG. 11, which includes a central opening 220 to receive the aerosol from the central aerosol delivery pathway 206 and an outer opening 222, which can be rotated to enable fluid communication with any one or two (if placed overlying a wall 212) of the outer segments in order to have a user-selected flavorant (or combination of flavorants) delivered to the oral cavity. Optionally, the mouth-end cap 216 can include a locking mechanism 230 to prevent rotation after a flavor is selected, such as a slide-activated lock that creates friction between the mouth-end cap 216 and another component of the housing 198 of FIG. 10. Various other locking mechanisms could be used, such as a magnetic lock, an interference lock, and the like. Alternatively, the mouth-end cap 216 could be removable and non-rotatable when affixed to the housing 198 such that the user must remove the cap to change the position of the outer opening 222 and then reattach the cap to the device.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
a first housing providing multiple aerosol pathways having a mouth-end with one or more openings through which aerosol can be inhaled by a user, the first housing defining a first aerosol delivery pathway in fluid communication with at least one of the one or more openings and a second aerosol delivery pathway separate from the first aerosol delivery pathway and in fluid communication with at least one of the one or more openings;
a reservoir located within the first housing or a second housing separate from the first housing, the reservoir containing a liquid aerosol precursor composition;
an atomizer located within the first housing or the second housing, the atomizer being in fluid communication with the reservoir, the atomizer adapted to produce a first aerosol from the liquid aerosol precursor composition, the atomizer positioned in fluid communication with the first aerosol delivery pathway, wherein the atomizer is in fluid communication with a first air inlet;
a flavorant-infused material positioned within the second aerosol delivery pathway and adapted to produce a second aerosol upon contact between the flavorant-infused material and flowing air, the flavorant-infused material positioned in fluid communication with a second air inlet.

2. The aerosol delivery device of claim 1, wherein the liquid aerosol precursor composition is substantially flavorant-free and optionally comprises nicotine.

3. The aerosol delivery device of claim 1, wherein the flavorant-infused material comprises a liquid solution or emulsion comprising a liquid carrier and a flavorant admixed with the liquid carrier, or comprises a substrate and a releasable flavorant carried by the substrate.

4. The aerosol delivery device of claim 1, wherein the flavorant-infused material is in the form of one or more porous monoliths, beads, particles, gels, capsules, and coatings.

5. The aerosol delivery device of claim 1, wherein the first housing further defines a mixing area downstream from the first and second aerosol delivery pathways and adapted to allow mixing of the first and second aerosols prior to exit from the one or more openings in the mouth-end.

6. The aerosol delivery device of claim 1, wherein the first housing comprises a plurality of different flavorant-infused materials, each flavorant-infused material positioned within a separate aerosol delivery pathway and in fluid communication with a separate air inlet.

7. The aerosol delivery device of claim 6, further comprising a mouth-end cap having first and second apertures, the first aperture downstream from, and in fluid communication with, the first aerosol delivery pathway and the second aperture downstream from, and in fluid communication with, at least one of the separate aerosol delivery pathways having a flavorant-infused material positioned therein.

8. The aerosol delivery device of claim 7, wherein the mouth-end cap is rotatable such that the user can move the second aperture into fluid communication with at least one of the separate aerosol delivery pathways having a flavorant-infused material positioned therein.

9. The aerosol delivery device of claim 6, further comprising a first aerosol delivery pathway and a plurality of separate aerosol delivery pathways, wherein a first opening is in fluid communication with the first aerosol delivery pathway and a plurality of different openings are in fluid communication with each of the plurality of separate aerosol delivery pathways having a flavorant-infused material positioned therein.

10. The aerosol delivery device of claim 1, wherein the atomizer is located within the second housing upstream from the first housing providing multiple aerosol pathways, the first housing providing multiple aerosol pathways being fixedly or removably attached to the separate second housing.

11. The aerosol delivery device of claim 1, wherein the first aerosol delivery pathway is centrally located within the first housing and the second aerosol delivery pathway is an annular region surrounding the first aerosol delivery pathway.

12. The aerosol delivery device of claim 11, wherein the annular region surrounding the first aerosol delivery pathway is divided into a plurality of separate aerosol delivery pathways, each containing a different flavorant-infused material and in fluid communication with a separate air inlet.

13. The aerosol delivery device of claim 12, further comprising a mouth-end cap having first and second apertures, the first aperture downstream from, and in fluid communication with, the first aerosol delivery pathway and the second aperture downstream from, and in fluid communication with, at least one of the separate aerosol delivery pathways having a flavorant-infused material positioned therein.

14. The aerosol delivery device of claim 13, wherein the mouth-end cap is rotatable such that the user can move the second aperture into fluid communication with different aerosol delivery pathways having a flavorant-infused material positioned therein.

15. The aerosol delivery device of claim 12, wherein a first opening is in fluid communication with the first aerosol delivery pathway and a plurality of different openings are in fluid communication with each of the plurality of separate aerosol delivery pathways having a flavorant-infused material positioned therein.

16. The aerosol delivery device of claim 1, further comprising a heater positioned to heat at least a portion of the flavorant-infused material positioned within the second aerosol delivery pathway.

17. The aerosol delivery device of claim 1, wherein the flavorant-infused material comprises a liquid solution or emulsion comprising a liquid carrier and a flavorant admixed with the liquid carrier, and wherein an aerosol jet array is positioned within the second aerosol delivery pathway to form droplets from the flavorant-infused material.

18. The aerosol delivery device of claim 1, wherein the atomizer is located within the housing providing multiple aerosol pathways.

19. The aerosol delivery device of claim 18, wherein the first aerosol delivery pathway and the second aerosol delivery pathway are in a side-by-side configuration within the first housing.

20. The aerosol delivery device of claim 1, wherein at least one breakable capsule containing an internal payload comprising a flavorant is positioned within the second aerosol delivery pathway.

21. The aerosol delivery device of claim 1, further comprising a rotatable absorbent material in fluid communication with a flavorant-infused material comprising a liquid solution or emulsion comprising a liquid carrier and a flavorant admixed with the liquid carrier, the rotatable adsorbent material adapted to produce droplets of the flavorant-infused material during rotation.

22. The aerosol delivery device of claim 1, wherein the first aerosol is respirable and the second aerosol is non-respirable.

23. The aerosol delivery device of claim 1, further comprising one or more of:

(a) an electrical power source located within the first housing or the second housing, the electrical power source configured to provide electrical current flow to the atomizer;

(b) a controller located within the first housing or the second housing, the controller adapted for controlling electrical current flow from the electrical power source; and (c) a flow sensor located within the first housing or the second housing, the flow sensor in communication with the controller and adapted to sense a pressure drop within the aerosol delivery device or a portion thereof.

* * * * *